(12) United States Patent
Grosvald Yaar Ad et al.

(10) Patent No.: US 12,303,337 B2
(45) Date of Patent: May 20, 2025

(54) PERINEAL PROTECTION DEVICE, SYSTEM AND METHOD

(71) Applicant: MOR RESEARCH APPLICATIONS LTD., Ramat Gan (IL)

(72) Inventors: Michal Grosvald Yaar Ad, Ramat Gan (IL); Idan Traistman, Ramat Gan (IL)

(73) Assignee: MOR RESEARCH APPLICATIONS LTD., Ramat Gan (IL)

( * ) Notice: Subject to any disclaimer, the term of this patent is extended or adjusted under 35 U.S.C. 154(b) by 349 days.

(21) Appl. No.: 17/792,493

(22) PCT Filed: Jan. 19, 2021

(86) PCT No.: PCT/IB2021/050370
§ 371 (c)(1),
(2) Date: Jul. 13, 2022

(87) PCT Pub. No.: WO2021/148933
PCT Pub. Date: Jul. 29, 2021

(65) Prior Publication Data
US 2023/0038075 A1 Feb. 9, 2023

Related U.S. Application Data

(60) Provisional application No. 62/963,380, filed on Jan. 20, 2020.

(51) Int. Cl.
*A61B 90/00* (2016.01)
*A61B 5/00* (2006.01)
(Continued)

(52) U.S. Cl.
CPC ............ *A61B 90/04* (2016.02); *A61B 5/4343* (2013.01); *A61F 5/24* (2013.01); *A61F 7/007* (2013.01);
(Continued)

(58) Field of Classification Search
CPC .............. A61B 90/04; A61B 5/4343; A61B 2017/00199; A61B 5/1075; A61B 5/1079;
(Continued)

(56) References Cited

U.S. PATENT DOCUMENTS 4,520,807 A 6/1985 Rotter
D702,836 S 4/2014 Haadem
(Continued)

FOREIGN PATENT DOCUMENTS

CN 201208289 Y 3/2009
CN 202342158 U 7/2012
(Continued)

OTHER PUBLICATIONS

"Alihosseni, Fatemeh, et al. "Investigating the effect of perineal heating pad on the frequency of episiotomies and perineal tears in primiparous females." Medical-Surgical Nursing Journal 7.1 (2018) Alihosseni, Fatemeh, et al. Aug. 4, 2018 (Aug. 4, 2018)".
(Continued)

*Primary Examiner* — Tarla R Patel
(74) *Attorney, Agent, or Firm* — The Roy Gross Law Firm, LLC; Roy D. Gross

(57) ABSTRACT

Aspects of embodiments pertain to a perineal protection device for reducing the risk or preventing perineal tear during birth. The device may comprise a reinforcement shield that is releasably connectable to a female perineum of a subject, the reinforcement shield having a surface geometry substantially corresponding to an underlying perineal muscle structure and being configured to reduce deformation of the perineum during childbirth. Optionally, the perineal protection device further comprises a fastener arrangement for releasably securing the reinforcement shield to the female perineum. The fastener arrangement may comprise a support pad that is adhesively engageable with the subject
(Continued)

and/or straps for strapping the reinforcement shield to the subject.

20 Claims, 4 Drawing Sheets

(51) Int. Cl.
  *A61B 17/00* (2006.01)
  *A61F 5/24* (2006.01)
  *A61F 7/00* (2006.01)
(52) U.S. Cl.
  CPC .............. *A61B 2017/00199* (2013.01); *A61F 2007/005* (2013.01)
(58) Field of Classification Search
  CPC ..... A61B 5/6823; A61B 5/6838; A61B 46/10; A61B 2017/00022; A61B 2017/00026; A61B 2017/00084; A61B 2017/00221; A61B 2090/064; A61B 17/42; A61F 7/007; A61F 2007/005; A61F 7/03; A61F 2007/0054; A61F 2007/0071; A61F 5/451; A61F 2007/0048
  See application file for complete search history.

(56) References Cited

U.S. PATENT DOCUMENTS

| | | |
|---|---|---|
| D854,683 S | 7/2019 | Haadem |
| 2007/0260163 A1 | 11/2007 | Blurton et al. |
| 2009/0148503 A1 | 6/2009 | Trieu |
| 2011/0022056 A1 | 1/2011 | Haadem |
| 2014/0276919 A1 * | 9/2014 | Blurton ..................... A61F 6/08 606/121 |
| 2015/0313636 A1 | 11/2015 | Shen et al. |
| 2016/0249848 A1 * | 9/2016 | Blurton ................... A61B 5/296 600/301 |
| 2018/0098790 A1 | 4/2018 | Odon |
| 2019/0125406 A1 * | 5/2019 | Heinberg ............... A61B 5/435 |

FOREIGN PATENT DOCUMENTS

| | | | |
|---|---|---|---|
| DE | 202014004862 U1 | 8/2014 | |
| EP | 2254487 B1 | 11/2011 | |
| GB | 1127548 A | 9/1968 | |
| WO | WO-2009101186 A1 * | 8/2009 | ............. A61B 17/42 |
| WO | 2011047066 A2 | 4/2011 | |
| WO | WO-2011072736 A1 * | 6/2011 | ............. A61B 17/42 |
| WO | WO-2016198551 A1 * | 12/2016 | ............. A61B 17/42 |
| WO | 2018130917 A1 | 7/2018 | |
| WO | WO-2019195097 A1 * | 10/2019 | ............. A61B 17/42 |

OTHER PUBLICATIONS

"Shek, K.L., Chantarasom, V., Langer, S. et al. Does the Epi-No® Birth Trainer reduce levator trauma? A randomised controlled trial. Int Urogynecol J 22, 1521-1528 (2011). https://doi.org/10.1007/s00192-011-1517-x".
"ISR & Written Opinion & Search Strategy for PCT/IB2021/050370".
"Ruckhäberle ,E. Jundt ,K. Baeuerle ,M.(2009) "Prospective randomised multicentre trial with the birth trainer EPI-NO® for the prevention of perineal trauma" Australian and New, Wiley Online Library".
"T. Lavesson et al. / European Journal of Obstetrics & Gynecology and Reproductive Biology 181 (2014) 10-14".

* cited by examiner

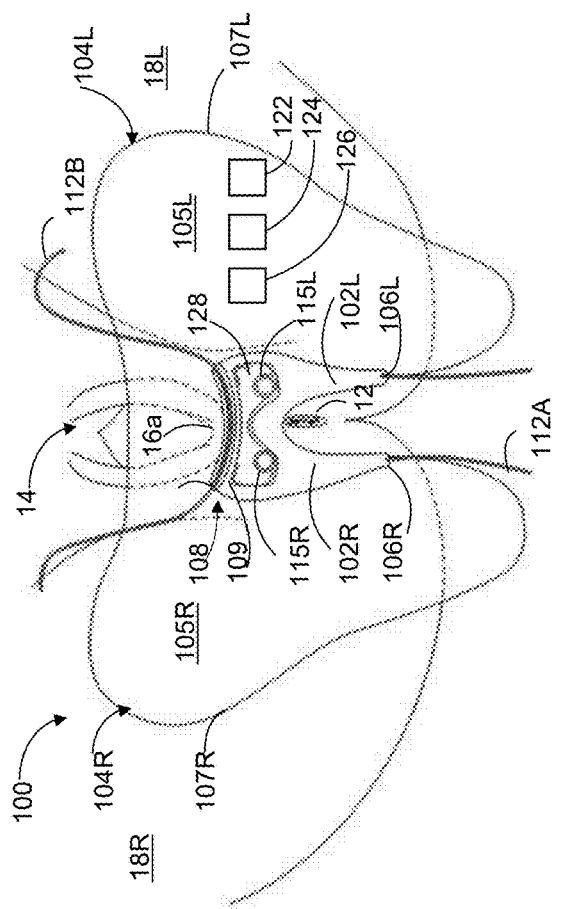
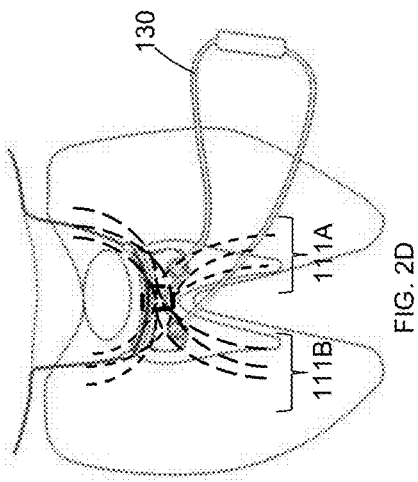
FIG. 2B
FIG. 2D
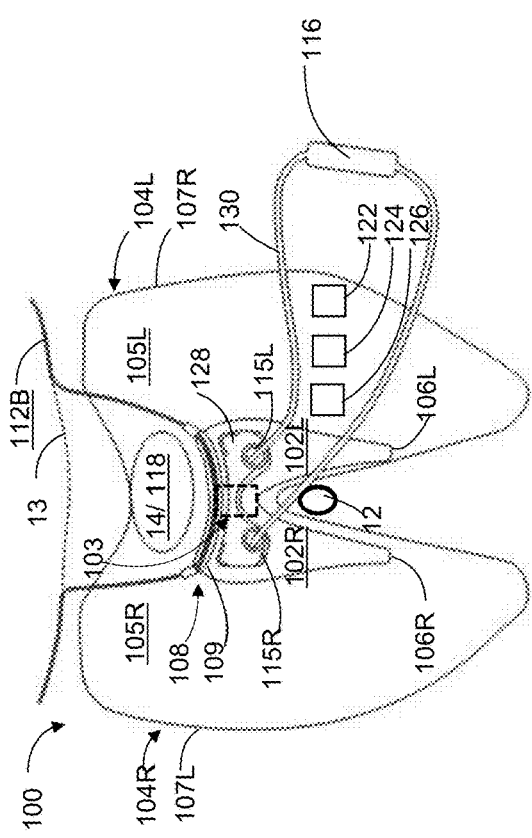
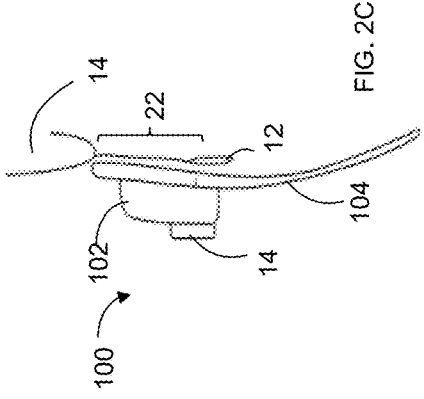
FIG. 2A
FIG. 2C though as one skilled in the art that the present invention may be practiced without these specific details. Furthermore, well-known methods, procedures, and components have not been omitted to highlight the invention.

PERINEAL PROTECTION DEVICE, SYSTEM AND METHOD

CROSS REFERENCE TO RELATED APPLICATIONS

This application is a National Phase of PCT Patent Application No. PCT/IB2021/050370 having International filing date of Jan. 19, 2021, which claims the benefit of priority of U.S. Provisional Patent Application No. 62/963,380, filed Jan. 20, 2020, the contents of which are all incorporated herein by reference in their entirety.

BACKGROUND

Obstetric anal sphincter injuries (OASIS) are caused by perineal trauma during vaginal delivery. Also referred to as third- and fourth-degree perineal lacerations, these injuries involve the anal sphincter complex and, in more severe cases, anal mucosa. In addition to contributing to short term perineal pain, OASIS is a leading risk factor for subsequent loss of bowel control in women.

There have been various solutions, however, all possess a particular deficiency. For example, vaginal dilatation devices are directed to expanding the vagina muscle walls to prevent OASIS. However, such devices do not provide the required perineum support.

Another approach is to insert a support device into the posterior portion of the vagina with suction cups that stick to the bottom wall of the vagina. However, this approach lacks an arcuate support surface to provide and direct the baby's head during crowning.

Therefore, there is a need to provide a perineal protection device operative to enhance tissue elasticity, provide support to tissue susceptible to tearing, and to redistribute forces generated during crowning while preserving access to medical personnel.

BRIEF DESCRIPTION OF THE DRAWINGS

The subject matter regarded as the invention is particularly pointed out and distinctly claimed in the concluding portion of the specification. The invention is best understood in view of the accompanying drawings in which:

FIGS. 2A-2B are schematic front view illustrations of a perineal protection device in a deployed state, according to an embodiment.

FIG. 2C is a schematic side view illustration of a perineal protection device in a deployed state, according to an embodiment.

FIG. 2D is a schematic illustration of reinforcement strings and/or fibers of a perineal protection device, according to an embodiment.

Figure 1A:
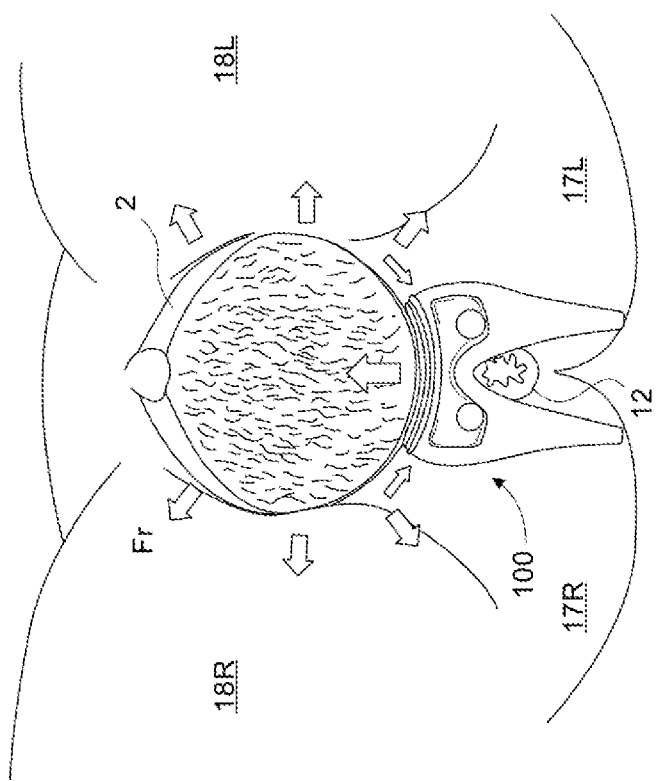
FIG. 1A is schematic illustration of crowning.

It will be appreciated that for the sake of clarity, elements shown in the figures may not be drawn to scale and reference numerals may be repeated in different figures to indicate corresponding or analogous elements.

DETAILED DESCRIPTION

In the following detailed description, specific details are set forth to facilitate understanding of the invention; however, it should be understood by those skilled in the art that the present invention may be practiced without these specific details. Furthermore, well-known methods, procedures, and components have not been omitted to highlight the invention.

Embodiments of the present invention are directed to perineal protection devices for mitigating, alleviating, or eliminating perineal trauma during vaginal delivery. Generally, this is accomplished by supporting the female perineum by operably engaging a perineal protection device with the female subject or person such that forces generated during, e.g., birth crowning, are redirected from areas susceptible to tearing and/or absorbed by the perineal protection device. Optionally, those areas susceptible to tearing are reinforced and, further optionally, their flexibility is increased.

In addition, the perineal protection device may slow down the exit pace of the infant's head to mitigate the likelihood of head burst and/or to prevent the need of performing episiotomy. Additionally, the protection device does not obstruct access of the vaginal cavity (e.g., with medical devices) when needed. For emergency procedures the protective device can be quickly removed.

It is noted that the expression "female perineum" may also encompass skin tissue portions in vicinity of (e.g., adjacent to and surrounding) the female perineum.

Figure 1B:
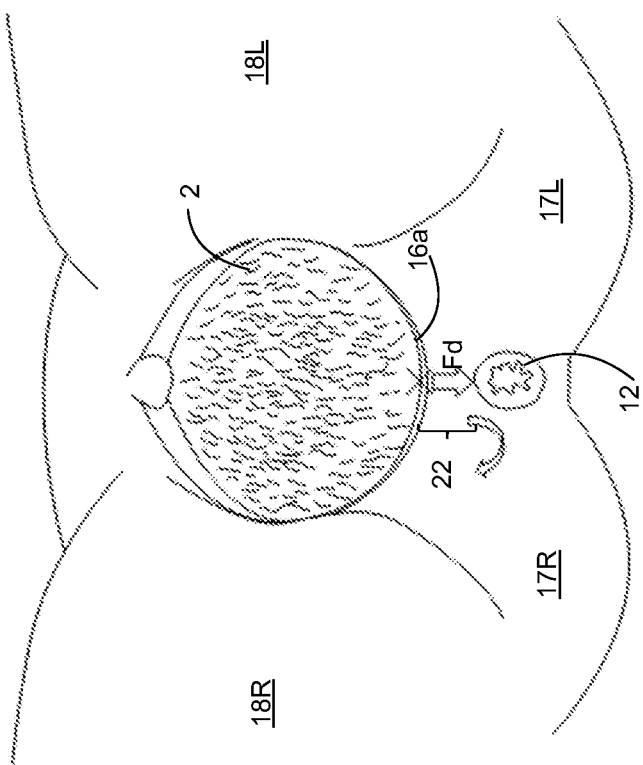
FIG. 1B is a schematic illustration of a perineal protection device in a deployed state during crowning, according to an embodiment.

FIGS. 1A and 1B are schematic views of stress forces that may be generated during crowning without deployment of a perineal protection device 100 (FIG. 1A), and the redistribution of crowning forces when protection device 100 is deployed to prevent perineal tearing (FIG. 1B). It is noted that the size and distribution of the forces shown in the Figures is for illustrative purposes only and should by no means construed in a limiting manner.

As shown, crowning of head 2 may generate a major force Fd downward onto posterior vaginal wall 16a when protection device 100 is not deployed. In contrast, when deployed, elements of protection device 100 provides support to posterior vaginal wall 16a, thereby causing redistribution and/or at least partial absorption of crowning forces (FIG. 1B) such to reduce the likelihood or prevent overstraining and, possibly, laceration of the subject's perineal area. For example, the major force Fd may be redistributed around the remaining vagina perimeter as forces Fr and/or absorbed by a reinforcement shield 102 and, optionally, further absorbed by an (e.g., adhesive) support pad 104 of protection device 100. The reinforcement shield and the support pad may be made of any suitable material having, for instance, sufficient elasticity to allow conformable engagement of the reinforcement shield and/or the support pad with the subject's perineal area and its surrounding regions and cause absorption and/or redistribution of forces generated in the perineal area during crowning to reduce the risk or to prevent perineal laceration. In some embodiments, the material may be stiff enough to obtain the effect of force redistribution and/or absorption yet elastic enough to optionally adjust its shape in response to changes in shape of the subject's anatomy (e.g., change of the shape of the perineal area and/or surrounding area).

Optionally, support pad may comprise various layers. Optionally, support pad may be configured to have a varying directional strength. For example, unidirectional strength may pertain to a configuration in which, e.g., the support pad, exhibits strength in one main direction, and bidirectional strength may pertain to a material configuration (e.g., fabric material configuration) exhibiting strength in two main different directions, etc. Optionally, material configuration of the support pad may be such to counteract forces imparted onto the perineal area during crowning.

In some embodiments, support pad 104 and/or reinforcement shield 102 may comprise (e.g., reinforcement) fibers and/or strings which are arranged in a repeating or non-repeating pattern (e.g., woven and/or otherwise arranged to form, for example, a mesh-like structure) such to obtain the desired directional strength characteristics, e.g., to counteract forces imparted onto the perineal area during crowning.

In some embodiments, reinforcement fibers/strings may be arranged to delineate an "X", to have a "chromosome-like" shape or be arranged to form an "8". A first set of fibers/strings may for example extend from the right side of the vagina to traverse or cross over the perineum body and extend to the left of and below the anus. A second set of fibers/strings may for example, correspondingly, extend from the left side of the vagina to traverse or cross over the perineum body and extend to the right side and below the anus. A junction between the strings may thus be formed by the two sets of strings/fibers between the vaginal opening and the anus. In some embodiments, reinforcement fibers/strings may delineate a generally, sinusoidal, wave-like or saw tooth pattern such that the fibers are expandable from a non-stretched to a stretched configuration when, for example, subjected to perineal shear forces. In the non-stretched state, the fibers may delineate a wave-like form of higher frequency and/or amplitude than in the stretched state.

Reference is now made to FIGS. 2A-C. Perineal protection device 100 includes a perineal reinforcement shield 102 for reinforcing a subject's perineum (also: perineal area or perineal body) 22 to prevent damage of the latter and, for example, support pad 104 (e.g., one or more right and left pad lobes 104R and 104L) for releasably attaching perineal reinforcement shield 102 to the perineal area. Optionally, pads 104R and 104L are also operable to provide additional support to the perineal area to prevent damage thereof. Such perineal damage prevention may not only include the actual prevention of laceration, but also to prevent overstraining of soft tissue structure of the perineal area and, optionally, of tissue structures surrounding the perineal area. It is noted that although "overstraining" may not necessarily cause perineal laceration, it could be a precursor or preliminary stage before possible perineal laceration.

Perineal reinforcement shield 102 may have the shape of "trousers" (i.e., trouser-shaped) and comprise right and left shield legs 102R and 102L that are extending, correspondingly, from a lower right/left shield leg end 106R/L. The lower left/right shield leg ends 106R/L, which may be extend, when protection device 100 is in a deployed state, below the anus 12 towards vaginal opening 14 of the subject to terminate in a "waistband" or upper edge support flange 108. Also, perineal reinforcement shield 102 has a lower surface geometry that arches around anus 12 when deployed, for example, to support sphincter muscles for preventing over-expansion of anus 12 by distributing forces exerted on the perineum during birth.

It is noted that the terms "right" and "left" as used herein pertain to the anatomical right and left side relative to the median plane of the subject with which the perineal protection device 100 is engaged. It is further noted that the expression "deployed state" pertains to a state in which the device is operably engaged with the subject for its intended purposes.

Support flange 108 may be sufficiently stiff to provide support for the baby's head during crowning. Support flange 108 may form a collar of sufficient width and extending distally away from the subject's vagina to support the infant's tissue, muscle, and/or skin, e.g., during crowning. In some embodiments, a padding element (not shown) may be disposed on the collar to support and protect the infant's tissue, muscle, skin and/or the subject's posterior vaginal wall 16a when the device is deployed. In some embodiments, support flange 108 provides support and guidance to the infant during crowning and reduces exit speed. The padding element can comprise, for example, rubber, silicon, cloth and/or any other soft or pliable material to increase patient comfort and to support and/or protect the subject and infant.

In some embodiments, support flange 108 may have an arcuate, straight or any other shape that may facilitate operable deployment of protection device 100. Optionally, support flange 108 may be change its shape in accordance with the vaginal opening during labor and achieve, for example, a (e.g., greatest arc) measure which is achieved by the posterior vaginal wall 16a during crowning. Optionally, support flange 108 may be stiff and have a shape that substantially corresponds to the greatest arc measure achieved by the posterior vaginal wall during crowning. Optionally, support flange 108 is implemented with a material having sufficient flexibility to increase in arc measure together the changing geometry of the posterior vaginal wall; yet, stiff enough to stabilize the posterior vaginal wall 16a of the subject to provide support to the infant head 2 during crowing and protect the perineum.

The right and left shield legs 102R and 102L regions are connected with each other, via a connecting portion 103, when protection device 100 is in a deployed state, above anus 12 and below vaginal opening 14. The boundaries of connecting portion 103 are schematically designated by dashed lines in FIG. 2A. Optionally, the right and left shield portions 102R and 102L may have an approximately triangular shape such to taper from the area of the connection portion 103 towards the lower right and left leg ends 102R and 102L, i.e., in a ventral-to-dorsal direction.

In some embodiments, support pad 104 may be implemented as a thin, flexible sheath forming right and left pad lobes 104R and 104L that may be positioned to cover, at least partially, the subject's buttocks 17R/L and/or right/left thighs 18R/L, accordingly. Support pad 104 may have an inner surface (not shown) for engaging with the subject's skin, and an outer surface 105 (e.g., right and left outer surface portions 105R and 105L) that is distal to the subject's skin relative to the inner surface, when the support pad 104 is operably engaged with the subject. Support pad 104 may have different thickness different locations, i.e., support pad may be thicker at a first location than at a second location. For example, the closer to the perineum, support pad thickness may increase. In some embodiments, support pad thickness may be substantially constant.

In some embodiments, perineal reinforcement shield 102 and support pad 104 may be partially or fully integrally formed with each other. In some embodiments, perineal reinforcement shield 102 and support pad 104 may be separate components that are fixedly or removably coupled with each other. In some embodiments, perineal reinforcement shield 102 may be fixedly coupled onto the outer surface of support pad 104. Right pad lobe 104R extends from right shield leg 102R, and left pad lobe 104L extends from left shield leg 102L to terminate in corresponding lobe boundaries 107R and 107L, optionally delineating "butterfly-shape".

In some embodiments, support pad 104 has a geometry corresponding to the anatomical geometry of the anatomical structure of the muscles underneath the skin of the perineum area and does not inhibit changes in muscle geometry during contraction.

In some embodiments, the inner surface of support pad 104 may be at least partially adhesive such to enable releasably fastening of the support pad to the subject's skin. Optionally, support pad 104 has low film or tensile strength of, for example, 10 psi or less.

In some embodiments, protection device 100 may comprise (e.g., at least partially elastic) a fastener arrangement 112, which may for example be implemented by straps, for securing protection device 100 to the subject's body (by strapping protection device the subject's thighs). Perineal reinforcement shield 102, which is coupled to the support pad 104, can be operably coupled to the subject's body for protecting the subject's perineal area or perineum.

In some embodiments, support pad 104 of perineal protection device 100 may comprise one or more straps 112 (e.g., such straps 112 may have lower strap portion 112A and upper strap portions 112B) for securing protection device 100 to the wearer when deployed.

For example, lower straps 112A may be employed for securing protection device 100 to a lower extremity (e.g., thighs and/or hip) of the subject when deployed, and upper strap portions 112B may be employed for securing protection device 100 to a higher extremity (e.g., abdomen) of the subject, when deployed.

Optionally, upper strap portion 112B may be positioned under the pregnant women's belly. When crowning occurs a part of the strap may be pulled and inserted into and/or under support flange 108 to secure the device, e.g., during crowning.

Strap ends of straps 112 may be coupled with each other and/or to the device via a suitable fastener such as, for example, Velcro®.

Protection device 100 may comprise loops, pins and/or holes or other strap-fastening and/or securing elements for (e.g., form-lockingly and/or frictionally) securing protection device 100 to the subject. For example, portion(s) of strap 112 can be traversed and/or inserted through loops, pins and/or holes for securing strap 112 to the subject. For example, support flange 108 may have a channel 109 through which upper strap portion 112B can traverse to secure protection device 100, when deployed, to the wearer, for instance, by coupling higher straps 112B with the subject's abdomen. For example, upper strap portion 112B may pass over the legs and connect to a pubis belt worn around by the subject around her pubis belt strip 13. Optionally, a pubis belt is configured to hold a clip and/or any other fastener for securing strap 112 to the subject. For example, strap 112 may be tied down and/or otherwise fastened with the subject, e.g., by tightly engaging a strap portion with flange 108, with a pubis belt of the subject, the subject's thighs, and/or the like.

In some embodiments, protection device 100 is configured such that when deployed, a portion of support pad 104 is positioned opposite vaginal opening 14 and implemented as a window 118 to enable medical personnel, e.g., vaginal, access for various medical procedures as needed including, for example, episiotomy, vacuum, clamps, and/or vaginal examination. Accordingly, perineum protection device 100 can be deployed during any type of delivery method and advantageously does not hinder medical procedures as noted above. Optionally, window 118 allows a medical professional to hold the infant's head 2 during crowning and, therefore, possibly allows reducing the exit speed of the infant.

In some embodiments, window may be implemented and/or covered by a transparent and (e.g., elastic and/or plastically deformable) sheath-like material for reducing exit speed of the infant while allowing, for example, episiotomy or other medical procedures. The transparent sheath-like material may be sufficiently elastic and/or thin to allow the infant to exit (yet at a comparatively lower pace). Optionally, the sheath material, when sufficiently stretched, tears or burst, for allowing for baby to exit. Optionally, the sheath material may have weakened areas for facilitating severing or tearing of the transparent sheath material. Optionally, a weakness area of the transparent sheath material can include, for example, a perforation line; an upper sheet portion removably fastened onto a lower wrapping member portion; a trench area formed in the at least one wrapping member; and/or the like. Optionally, the weakness area may be selectively thinner compared to other areas of the at least one wrapping member. Optionally, the transparent sheath material may be severed by the forces imparted by the baby's head onto the sheath during crowning. Optionally, the transparent window may be elastic yet strong enough to stretch over the baby's head during crowning (e.g., up to a certain extent) without being severed by the forces imparted by the baby's head onto the sheath material during crowning. Optionally, the transparent window can be peeled off the baby's head.

In some embodiments, perineal protection device 100 may comprise sensors 122 that are configured and positioned for sensing various physical quantities and/or changes of tissue-related characteristics including, for example, temperature of the perineal area, magnitude, direction and/or location of shear and/or normal stress to which the perineal area may be subjected to (e.g., during crowning); sensors (e.g., light-based sensors) for measuring thickness of the underlying subcutaneous perineal tissue, anal sphincter, pelvic floor, and/or the like. For example, sensors 122 may comprise an electroactive (e.g., polymer) material that outputs an electric signal responsive to material deformation. Optionally, a measured magnitude in material deformation may be translated into a shear stress and/or normal stress measurement.

Based on the output provided by sensors 122 to controller 202 (e.g., based on a voltage output or change voltage output by electroactive material in response to tissue deformation), tissue-related characteristics of the perineal area may be monitored by outputs provided by sensors 122.

In some embodiments, perineal protection device 100 may comprise actuators 124 for causing the actuation of various shield functionalities comprising, for example, changing mechanical characteristic of protective shield portions including, e.g., stiffness, elasticity, flexibility and/or shape of reinforcement shield 102 (e.g., of support flange 108) and/or support pad 104, for example, upon receipt of a controller signal that may be output by controller 202.

The controller signal, for instance, may cause the electroactive material to reshape, stiffen, relax and/or otherwise selectively and locally change mechanical characteristics (e.g., stiffness, elasticity and/or flexibility), to counteract deformation of perineal area 22 and/or to (e.g., increasingly or decreasingly) absorb stress to which perineal area 22 may be subjected to for reducing the risk or to prevent perineal laceration.

Accordingly, the electroactive material may in some embodiments act as a sensor 122, as an actuator 124, or both. Optionally, a first portion of electroactive material may act as a sensor, and another portion as actuator. Optionally, the same portions of electroactive material may act as a sensor and as an actuator.

In some embodiments, protection device 100 may be configured to allow heating of the subject's perineal area. Heating of perineal area 22 increases elasticity of the area by enhancing local blood flow and the resulting oxygenation, thereby reducing the possibility of tearing. For instance, protection device 100 may be configured such that portions thereof are heatable.

In some embodiments, the fibers/strings may be configured (e.g., comprise material) that generates heat responsive to stretching. For example, stretching of the fibers/strings may increase the temperature of material contained in the fibers/strings, e.g., to a desired temperature. Conversely, relaxing the fiber/strings may decrease the temperature.

In some embodiments, protection device 100 may comprise a (e.g., controllable) heating apparatus 126 arranged to allow heating of the subject's perineal area. Heating apparatus 126 may comprise a heating arrangement 128 including, for example, an electrical heater, a receptacle for receiving a heating and/or cooling fluid (e.g., liquid, air and/or gas), and/or a conduit 130 (cf. FIG. 2A) through which a heating and/or cooling fluid can circulate for heating and/or cooling perineal area 22. Optionally, conduit 130 may traverse through ports 115R and 115L. Heating/cooling of the fluid may be controllable via a user control interface 116. In some embodiments, the fibers/strings may be controllably heatable. In some embodiments, the electrical heater may be implemented (fully or partially) by the fibers/strings.

In some examples, fluid may circulate via ports 115R/L for heating portions of protection device 110. Optionally, the fluid may be heatable (e.g., by electrical heating elements) to about 35 C degrees or higher. Optionally, the fluid may circulate in a steady state manner through the conduit. In some embodiments, heat may be provided to the fluid and/or perineal area, directly or indirectly, by the electrical heating elements embedded in protection device 100.

In some embodiments, heating apparatus 126 may comprise an electrical heater, a heat pump, valve actuators 124 and/or a pump for controlling circulation of a heating fluid in a fluid conduit, and/or the like. Optionally, perineal reinforcement shield 102 is in thermal communication with a heating arrangement 128 from which heat is transferred, directly or indirectly, to perineal area 22. For example, heat may be transferred through reinforcement shield 102 and/or support pad 104 to perineal area 22.

In some embodiments, based on the monitored tissue-related characteristics, heating, cooling and/or other measures such as change in mechanical characteristics of the electroactive material may be implemented to reduce the risk or to prevent perineal tear. Optionally, reinforcement shield 102 and/or support pad 104 may comprise such electroactive material.

In some embodiments, heating apparatus 126 may be controlled by controller 202 by a device control engine based on the output provided by sensors 122. For example, perineal area 22 may be heated and/or cooled to obtain a desired temperature of perineal area 22 and, accordingly, obtain a desired elasticity and/or softness of the perineal area.

The term "engine" and "module" may comprise one or more computer modules, wherein a module may be a self-contained hardware and/or software component that interfaces with a larger system. A module may comprise a machine or machines executable instructions. A module may be embodied by a circuit or a controller programmed to cause the system to implement the method, process and/or operation as disclosed herein. For example, a module may be implemented as a hardware circuit comprising, e.g., custom VLSI circuits or gate arrays, an Application-specific integrated circuit (ASIC), off-the-shelf semiconductors such as logic chips, transistors, and/or other discrete components. A module may also be implemented in programmable hardware devices such as field programmable gate arrays, programmable array logic, programmable logic devices and/or the like.

In some embodiments, heating apparatus 126 may comprise, for example, an electrical heater, a conduit for hot fluid, cold fluid and/or the like. The hot fluid may be heated, for example, by an electrical heater and/or by a substance mixture (e.g., comprised in protection device 100) and which is actionable to generate heat in an exothermic chemical reaction for heating fluid that is present in a hot fluid flow path or hot fluid receptacle of protection device 100. In some embodiments, heat is provided to perineal area 22 conductively by an exothermic chemical reaction, without employing a fluid for transferring heat generated by the chemical reaction.

In some examples, at least some portions of protection device 100 may comprise heat conductive material (e.g., natural rubber, PVC) to facilitate (e.g., conductive) heat transfer from (not shown) to the underlying tissue of the subject. For example, reinforcement shield 102 and support pad 104 may heat the conductive material.

As mentioned above, the support pad may comprise (e.g., reinforcement) fibers and/or strings which are arranged in a repeating or non-repeating pattern (e.g., woven and/or otherwise arranged to form, for example, a mesh-like structure) such to obtain a desired (e.g., varying) directional strength characteristics, e.g., to counteract forces imparted onto the perineal area during crowning. For example, as shown schematically in FIG. 2D, reinforcement fibers/strings 111 may be arranged such that when device 100 is operably engaged, they delineate an "X", or to have a "chromosome-like" shape or be arranged to form an "8", have a crisscross configuration, and/or the like. A first set of fibers/strings 111A (indicated by short and dashed curves) may for example extend from the right side of the vagina to traverse or cross over the perineum body and extend to the left of and below the anus. A second set of fibers/strings 111B (indicated by long dashed curves) may for example, correspondingly, extend from the left side of the vagina to traverse or cross over the perineum body and extend to the right side and below the anus. A junction between the strings may thus be formed by the two sets of strings/fibers 111A and 111B between the vaginal opening and the anus. The fibers/strings may have additional or alternative configurations (e.g., delineate additional or alternative patterns and/or geometric outlines) than what is described herein and schematically illustrated in FIG. 2D.

In some embodiments, protection device 100 may comprise a device power source (not shown) for powering the various components of protection device such as, for example, electrical heaters.

Figure 3:
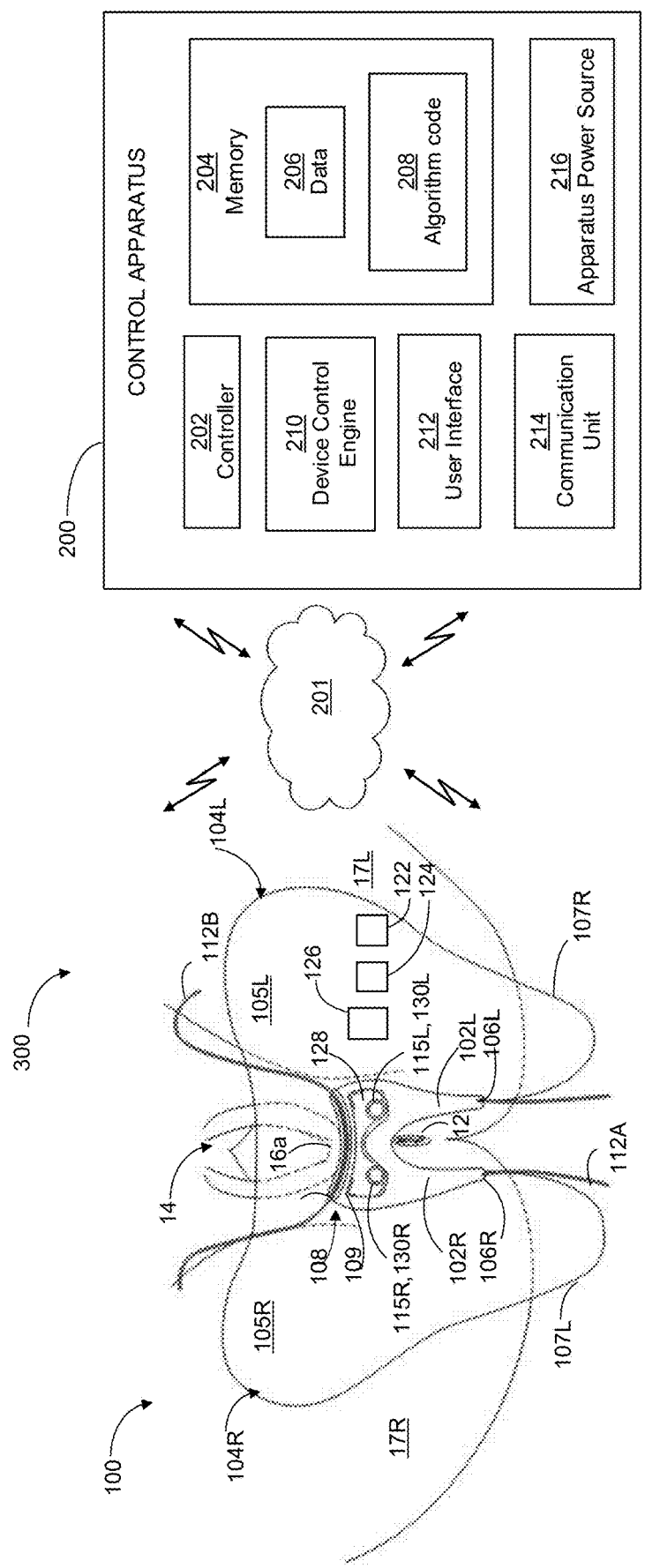
FIG. 3 is a schematic illustration of a perineal protection system, according to an embodiment.

As shown in FIG. 3, sensors 122, actuators 124 and heating apparatus 126 may be communicably coupled with a control apparatus 200 via (wired and/or wireless) communication links of a network 201 for controlling the sensors, actuators and/or the heating apparatus. Perineal protection device 100 and control apparatus 200 may define a perineal protection system 300.

Control apparatus 200 may be included or implemented by a multifunction mobile communication device also known as "smartphone", a personal computer, a laptop computer, a tablet computer, a server (which may relate to one or more servers or storage systems and/or services associated with a business or corporate entity, including for example, a file hosting service, cloud storage service, online file storage provider, peer-to-peer file storage or hosting service and/or a cyberlocker), personal digital assistant, a workstation, a wearable device, a handheld computer, a notebook computer, a vehicular device, a stationary device and/or a home appliances control system.

Control apparatus 200 may comprise an (e.g., processor-based) controller 202, a memory 204 for storing software including processing data 206 and algorithm code 208.

Controller 202 executing algorithm code 208, optionally in conjunction with data 206, may cause the execution of the method, process and/or operation of monitoring a perineal area and/or controlling functionalities of the perineal protection device 100. Such methods, processes and/or operations may herein be implemented by a device control engine 210.

The term "controller", as used herein, may additionally or alternatively refer to a processor. A processor may be implemented by various types of processor devices and/or processor architectures including, for example, embedded processors, communication processors, graphics processing unit (GPU)-accelerated computing, soft-core processors and/or general purpose processors.

According to some embodiments, memory 204 may include one or more types of computer-readable storage media. Memory 204 may include, for example, transactional memory and/or long-term storage memory facilities and may function as file storage, document storage, program storage, or as a working memory. The latter may for example be in the form of a static random access memory (SRAM), dynamic random access memory (DRAM), read-only memory (ROM), cache and/or flash memory. As working memory, memory 204 may, for example, include temporally-based and/or non-temporally based instructions. As long-term memory, memory 204 may for example include a volatile or non-volatile computer storage medium, a hard disk drive, a solid state drive, a magnetic storage medium, a flash memory and/or other storage facility. A hardware memory facility may for example store a fixed information set (e.g., software code) including, but not limited to, a file, program, application, source code, object code, data, and/or the like.

In some embodiments, device control may be fully automatic or semi-automatic. For example, based on a sensor output provided by sensors 122 and received by controller 202, the controller 202 may control actuator 124 and/or regulate the operation of heating apparatus 126.

It is noted that although components and/or modules of control apparatus 200 may be shown as being separate from protection device 100 (e.g., implemented in a mobile communication device), they may be partially or fully implemented by components and/or modules which are comprised in protection device 100 (e.g., embedded in support pad 104 and/or in any other parts of protection device 100). For instance, separate controllers, processors and memories may be allocated to implement a device control engine 210. However, for simplicity, the following description may herein refer, for example, generically to controller 202 and memory 204 for implementing device control engine 210 and/or other functions of perineal protection system 300.

In some embodiments, outputs provided by sensors 122 may be analyzed by device control engine 210 for determining whether the subject's perineal area is about to lacerate or not. If the performed analysis meets a warning output criterion, control apparatus 200 may provide an output indicative of an imminent danger of laceration. If the performed analysis does not meet a warning output criterion, control apparatus 200 may provide an analysis output indicative of no imminent danger of perineal laceration. Based on the analysis output, controller 202 may control actuator 124 (e.g., the output provided to electroactive material) and/or regulate the operation of heating apparatus 126.

In some embodiments, device control engine 210 may optionally be controllable by a user providing, for example via a user interface 212, command inputs for controlling various device functionalities. User interface 212 may include input and/or output devices such as, for example, a computer display, a touch screen, a keyboard, a mouse, a keypad, a mouse, a touch-pad, a track-ball, a stylus, a microphone, audio speakers, earphones and/or the like.

Control apparatus 200 may further comprise a communication unit 214 for allowing the transmission of control signals to hardware components such as a controller (not shown) of heating apparatus 126 and/or actuators 124. Communication unit 214 may include, for example, include I/O device drivers (not shown) and network interface drivers (not shown) for enabling the transmission and/or reception of data over network 201. A device driver may for example, interface with a keypad or to a USB port. A network interface driver may for example execute protocols for the Internet, or an Intranet, Wide Area Network (WAN), Local Area Network (LAN) employing, e.g., Wireless Local Area Network (WLAN)), Metropolitan Area Network (MAN), Personal Area Network (PAN), extranet, 2G, 3G, 3.5G, 4G including for example Mobile WIMAX or Long Term Evolution (LTE) advanced, Bluetooth® (e.g., Bluetooth smart), ZigBee™, near-field communication (NFC) and/or any other current or future communication network, standard, and/or system.

Control apparatus 200 may further comprise an apparatus power source 216 for powering the various components of control apparatus 200.

In some embodiments, perineum protection device 100 can be provided as part of a kit including an alcohol pad, razor, sticker, a topical formulation (e.g., a powder, a lotion, a cream, an ointment, a wipe, a sponge, a solution, an emulsion, a paste, a gel, a patch, a swab, mousses, a dressing, and/or a pad, e.g., to reduce skin irritation and/or heating apparatus 126 (or components thereof).

Figure 4:
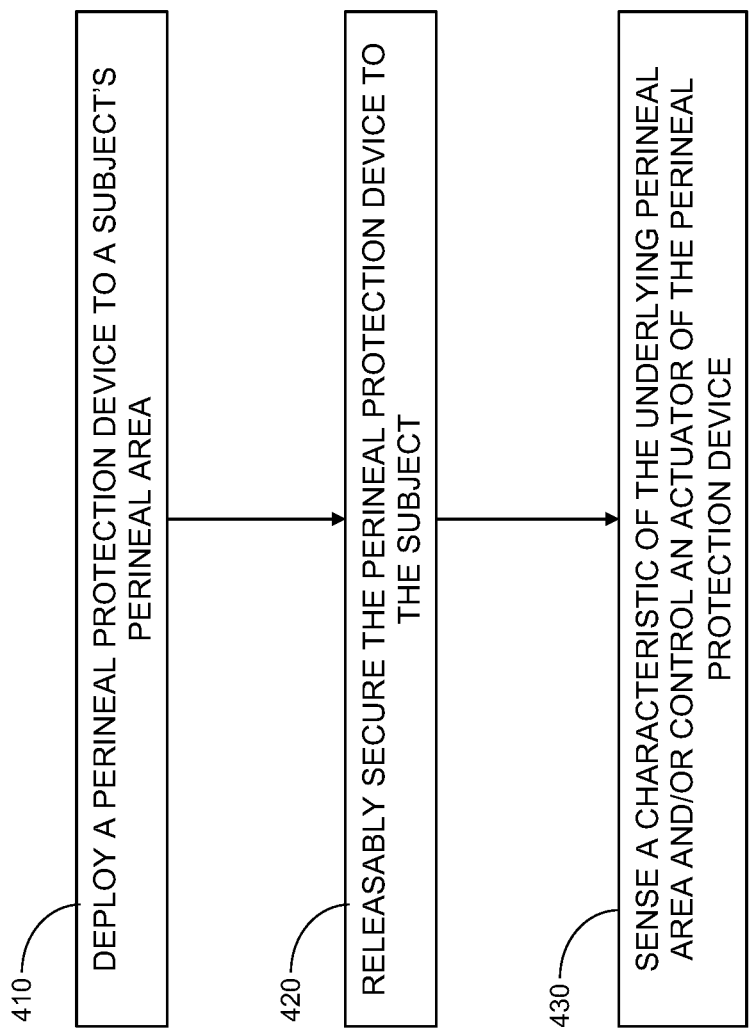
FIG. 4 is a flow chart of a method for protecting a perineum, according to an embodiment.

Referring now to FIG. 4, a method for protecting a perineal area 22 may comprise arranging or deploying (e.g., operably engaging) perineal protection device 100 with a perineal area of a subject (block 410). Optionally, to deploy, the perineum area may be shaved and/or cleaned, prior to deploying support pad 104. Support pad 104 may be arranged engaged with perineum 22 in alignment with underlying muscle direction and lower part of the subject's groin such that window 118 is positioned opposite vaginal opening 14.

In some embodiments, support pad 104 may be first be applied to the subject, and then reinforcement shield 102 may be securely coupled (e.g., glued or otherwise fastened) to the pad such that the lower portion of reinforcement shield 102 arches above anus 12 on the perineum.

In some embodiments, reinforcement shield 102 may be releasably secured to support pad 104 such that the lower portion of reinforcement shield 102 arches above anus 12 on the perineum.

The method may further include, for example, releasably securing perineal protection device 100 to the subject (block 420). For example, protection device 100 may be glued or strapped to the subject. For instance, pad 104 may be glued to the subject using an adhesive.

Optionally, the arc measure of the lower arch of reinforcement shield 102 increase as anus 12 expands during delivery. This size increase allows fecal matter and other secretions to exit the area without soiling the mother and/or reinforcement shield 102. In a certain embodiment, legs extending from the arch of reinforcement shield 102 are constructed from rubber or other flexible materials so minimize discomfort while sitting on the birthing chair.

In some embodiments, the method may further include, for example, sensing a characteristic of the underlying perineal area and/or controlling an actuator of the perineal protection device (block 430). Optionally, an actuator may be controlled based on a sensed characteristic of the underlying perineal area.

For example, as noted above, electroactive material (e.g., polymer) 120 may in a certain configuration be operative to generate an electrical signal responsively to deformation caused by deformation of the perineum. Based on the electrical signal, Controller 202 may provide an output to a user interface to enable appropriate course of action. In another configuration, electroactive material may be configured to change its shape (e.g., thickness and/or geometric contour) and/or mechanical characteristics (e.g., flexibility, elasticity and/or stiffness) responsively to a controller signal issued in accordance with detected perineal deformation. Controller 202 can issue a signal in response to a manual input through user interface and/or through automated input like additional electroactive material configured to issue a signal responsively to detected deformation.

ADDITIONAL EXAMPLES

Example 1 pertains to a perineal protection device for reducing perineal tear during birth, the device comprising: a reinforcement shield that is releasably connectable to a female perineum, the reinforcement shield having a surface geometry substantially corresponding to an underlying perineal muscle structure and being configured to reduce deformation of the perineum during childbirth.

Example 2 includes the subject matter of Example 1 and, optionally, further comprising a fastener arrangement for releasably securing the reinforcement shield to the female perineum.

Example 3 includes the subject matter of Example 2 and, optionally, wherein the fastener arrangement comprises a support pad that is adhesively engageable with the subject and/or straps for strapping the reinforcement shield to the subject when deployed.

Example 4 includes the subject matter of Example 3 and, optionally, wherein the reinforcement shield is couplable with the support pad.

Example 5 includes the subject matter of any one or more of the Examples 1 to 4 and, optionally, wherein the reinforcement shield includes an arcuate support flange configured to support a posterior vaginal wall when deployed.

Example 6 includes the subject matter of any one or more of the Examples 1 to 5 and, optionally, wherein the reinforcement shield includes an arcuate support flange has an arc measure corresponding to a greatest arc measure achieved by the posterior vaginal wall during crowning.

Example 7 includes the subject matter of any one or more of the Examples 1 to 6 and, optionally, wherein the reinforcement shield includes an arcuate support flange has an arc measure that changes in accordance with a change in the posterior vaginal wall during crowning.

Example 8 includes the subject matter of any one or more of the Examples 1 to 7 and, optionally wherein the reinforcement shield has a lower arcuate geometry arching the anus of a wearer when deployed.

Example 9 includes the subject matter of any one or more of the Examples 1 to 8 and, optionally, further comprises a heating apparatus for transferring heat to the perineum.

Example 10 includes the subject matter of any one or more of the Examples 1 to 9 and, optionally, wherein the heating apparatus comprises a heating body that is in thermal communication with the reinforcement shield for transferring heat from the heating body, via the reinforcement shield, to the perineum.

Example 11 includes the subject matter of any of the Examples 9 or 10 and, optionally, wherein the heating apparatus comprises an electrical heating element, a heating liquid, and/or a chemical heater.

Example 12 includes the subject matter of any one or more of the Examples 1 to 11 and, optionally, further comprises electroactive material that is in communication with a controller and configured to emit a signal responsively to sensing of a perineum deformation.

Example 13 includes the subject matter of Example 12 and, optionally, wherein the reinforcement shield and/or the support pad comprises or consists of the electroactive material.

Example 14 includes the subject matter of Example 13 and, optionally, wherein the heating apparatus is actuated by a controller responsively to detection of perineal deformation.

Example 15 includes the subject matter of any one or more of the Examples 1 to 14 and, optionally, further comprises an actuator that is controlled by a controller.

Example 16 includes the subject matter of Example 15 and, optionally, further comprises a sensor for monitoring a characteristic of the perineum.

Example 17 includes the subject matter of Example 16 and, optionally, wherein the actuator is controlled by a controller based on signals received by the sensor.

Example 18 includes the subject matter of any one or more of the Examples 15 to 17 and, optionally, wherein the actuator is implemented by or comprises electroactive material.

Example 19 includes the subject matter of Example 18 and, optionally, wherein the controller is operable to change a material characteristic of the electroactive material.

Example 20 includes the subject matter of Example 19 and, optionally, wherein the material characteristics includes stiffness, flexibility, and/or a surface geometry of a structure formed by the material.

Example 21 includes the subject matter of any one or more of the Examples 1 to 20 and, optionally, wherein the characteristic of the perineum comprises temperature, shear stress, normal stress, subcutaneous tissue thickness, and/or perineal deformation.

Example 22 includes the subject matter of any one or more of the Examples 2 to 21 and, optionally, the e.g., adhesive, support pad is implemented as an electroactive-polymer support pad in communication with a controller, the electroactive-polymer pad configured to stiffen responsively to receipt of controller signal issued by the controller.

As used herein, the phrase "A,B,C, or any combination of the aforesaid" should be interpreted as meaning all of the following: (i) A or B or C or any combination of A, B, and C, (ii) at least one of A, B, and C; and (iii) A, and/or B and/or C. This concept is illustrated for three elements (i.e., A,B,C), but extends to fewer and greater numbers of elements (e.g., A, B, C, D, etc.).

Wherever applicable, the phrase "selected from the group consisting of A, B, and C" can replace the phrase "A,B,C, or any combination of the aforesaid".

The terms "engine", "module", "applications" and/or "system" as used herein in the context of computerized functionalities may comprise one or more computer modules. Exemplarily, a module may be a self-contained hardware and/or software component that interfaces with a larger system. A module may comprise a machine or machines (also: computer-) executable program instructions. A module may be embodied by a circuit or a controller programmed to cause the system to implement the method, process and/or operation as disclosed herein. For example, a module may be implemented as a hardware circuit comprising, e.g., custom Very Large Scale Integrated (VLSI) circuits or gate arrays, an Application-specific integrated circuit (ASIC), off-the-shelf semiconductors such as logic chips, transistors, and/or other discrete components. A module may also be implemented in programmable hardware devices such as field programmable gate arrays, programmable array logic, programmable logic devices and/or the like.

Any digital computer system, module and/or engine exemplified herein can be adapted or configured or otherwise programmed to implement a method disclosed herein, and to the extent that the system, module and/or engine is operable to implement such a method, it is within the scope and spirit of the disclosure. Once the system, module and/or engine are programmed to perform particular functions pursuant to computer readable and executable program instructions from program software that implements a method disclosed herein, it in effect becomes a special purpose computer particular to embodiments of the method disclosed herein. The methods and/or processes disclosed herein may be implemented as a computer program product that may be tangibly embodied in an information carrier including, for example, in a non-transitory tangible computer-readable and/or non-transitory tangible machine-readable storage device. The computer program product may be directly loadable into an internal memory of a digital computer, comprising software code portions for performing the methods and/or processes as disclosed herein.

Additionally, or alternatively, the methods and/or processes disclosed herein may be implemented as a computer program that may be intangibly embodied by a computer readable signal medium. A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a non-transitory computer or machine-readable storage device and that can communicate, propagate, or transport a program for use by or in connection with apparatuses, systems, platforms, methods, operations and/or processes discussed herein.

The terms "non-transitory computer-readable storage device" and "non-transitory machine-readable storage device" encompasses distribution media, intermediate storage media, execution memory of a computer, and any other medium or device capable of storing for later reading by a computer program implementing embodiments of a method disclosed herein. A computer program product can be deployed to be executed on one computer or on multiple computers at one site or distributed across multiple sites and interconnected by one or more communication networks.

These computer readable and executable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable and executable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable and executable program instructions may also be loaded onto a computer, other programmable data processing apparatus, or other device to cause a series of operational steps to be performed on the computer, other programmable apparatus or other device to produce a computer implemented process, such that the program instructions which execute on the computer, other programmable apparatus, or other device implement the functions/acts specified in the flowchart and/or block diagram block or blocks.

In the discussion, unless otherwise stated, adjectives such as "substantially" and "about" that modify a condition or relationship characteristic of a feature or features of an embodiment of the invention, are to be understood to mean that the condition or characteristic is defined to within tolerances that are acceptable for operation of the embodiment for an application for which it is intended.

"Coupled with" means indirectly or directly "coupled with".

It is important to note that the method may include is not limited to those diagrams or to the corresponding descriptions. For example, the method may include additional or even fewer processes or operations in comparison to what is described in the figures. In addition, embodiments of the method are not necessarily limited to the chronological order as illustrated and described herein.

Discussions herein utilizing terms such as, for example, "processing", "computing", "calculating", "determining", "establishing", "analyzing", "checking", "estimating", "deriving", "selecting", "inferring" or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store computer-executable program instructions to perform operations and/or processes. The term determining may, where applicable, also refer to "heuristically determining".

It should be noted that where an embodiment refers to a condition of "above a threshold", this should not be construed as excluding an embodiment referring to a condition of "equal or above a threshold". Analogously, where an embodiment refers to a condition "below a threshold", this should not to be construed as excluding an embodiment referring to a condition "equal or below a threshold". It is clear that should a condition be interpreted as being fulfilled if the value of a given parameter is above a threshold, then the same condition is considered as not being fulfilled if the value of the given parameter is equal or below the given threshold. Conversely, should a condition be interpreted as being fulfilled if the value of a given parameter is equal or above a threshold, then the same condition is considered as not being fulfilled if the value of the given parameter is below (and only below) the given threshold.

It should be understood that where the claims or specification refer to "a" or "an" element and/or feature, such reference is not to be construed as there being only one of that element. Hence, reference to "an element" or "at least one element" for instance may also encompass "one or more elements".

Terms used in the singular shall also include the plural, except where expressly otherwise stated or where the context otherwise requires.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

As used herein, if a machine (e.g., a controller, or a processor in conjunction with a memory) is described as "operable to" perform a task, then, at least in some embodiments, the machine may include components, parts, or aspects (e.g., software) that enable the machine to perform a particular task. In some embodiments, the machine may perform this task during operation. Similarly, when a task is described as being done "in order to" establish a target result, then, at least in some embodiments, carrying out the task may accomplish the target result.

It is noted that the terms "operable to" can encompass the meaning of the term "adapted or configured to". In other words, a machine "operable to" perform a task can in some embodiments, embrace a mere capability (e.g., "adapted") to perform the function and, in some other embodiments, a machine that is actually made to (e.g., "configured") to perform the function.

Unless otherwise stated, the use of the expression "and/or" between the last two members of a list of options for selection indicates that a selection of one or more of the listed options is appropriate and may be made, and may be used interchangeably with the expressions "at least one of the following", "any one of the following" or "one or more of the following", followed by the listing of the options.

It is appreciated that certain features of the invention, which are, for clarity, described in the context of separate embodiments or example, may also be provided in combination in a single embodiment. Conversely, various features of the invention, which are, for brevity, described in the context of a single embodiment, example and/or option, may also be provided separately or in any suitable sub-combination or as suitable in any other described embodiment, example or option of the invention. Certain features described in the context of various embodiments, examples and/or optional implementation are not to be considered essential features of those embodiments, unless the embodiment, example and/or optional implementation is inoperative without those elements.

The number of elements shown in the Figures should by no means be construed as limiting and is for illustrative purposes only.

Throughout this application, various embodiments may be presented in and/or relate to a range format. It should be understood that the description in range format is merely for convenience and brevity and should not be construed as an inflexible limitation on the scope of the embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Where applicable, whenever a numerical range is indicated herein, it is meant to include any cited numeral (fractional or integral) within the indicated range.

The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

It should be appreciated that embodiments formed from combinations of features set forth in separate embodiments are also within the scope of the present invention.

While certain features of the invention have been illustrated and described herein, modifications, substitutions, and equivalents are included within the scope of the invention.

What is claimed is:

1. A perineal protection device adapted for preventing perineal tear during birth, the device comprising:
    a) a reinforcement shield and a support pad that are adapted for releasably connectable to a female perineum of a subject, the reinforcement shield having a surface geometry substantially corresponding to an underlying perineal muscle structure and being configured to reduce deformation of the perineum during childbirth; and
    b) wherein the reinforcement shield and the support pad are configured to have reinforcement fibers of varying directional strength in at least two different directions; and
    c) at least one sensor including a shear force sensor configured for detecting at least one of: magnitude, direction or location of the shear force;
    d) an electroactive material that is in communication with a controller; and wherein the electroactive material is configured to emit a signal responsively to sensing of shear force or a perineum deformation; and wherein the electroactive material is configured to render a change in at least one mechanical characteristic selected form: stiffness, elasticity, flexibility, shape, thickness, or geometric contour and wherein the electroactive material is featured in at least one of the support pad or the reinforcement shield.

2. The perineal protection device of claim 1, further comprising a fastener arrangement for releasably securing the reinforcement shield to the female perineum.

3. The perineal protection device of claim 2, wherein the fastener arrangement comprises a support pad that is adhesively engageable with the subject and/or straps for strapping the reinforcement shield to the subject when deployed.

4. The perineal protection device of claim 3, wherein the support pad of the fastener arrangement is implemented as an electroactive-polymer support pad in communication with a controller, the electroactive-polymer support pad is configured to stiffen responsively to receipt of controller signal issued by the controller.

5. The perineal protection device of claim 1, wherein the reinforcement shield is couplable with the support pad.

6. The perineal protection device of claim 1, wherein the reinforcement shield includes an arcuate support flange configured to support a posterior vaginal wall when deployed.

7. The perineal protection device of claim 1, wherein the reinforcement shield includes an arcuate support flange has an arc measure corresponding to a greatest arc measure achieved by the posterior vaginal wall during crowning.

8. The perineal protection device of claim 1, wherein the reinforcement shield includes an arcuate support flange has an arc measure that changes in accordance with a change in the posterior vaginal wall during crowning.

9. The perineal protection device of claim 1, wherein the reinforcement shield has a lower arcuate geometry arching an anus of the subject.

10. The perineal protection device of claim 1, further comprising a heating apparatus for transferring heat to the perineum.

11. The perineal protection device of claim 10, wherein the heating apparatus comprises a heating body that is in thermal communication with the reinforcement shield for transferring heat from the heating body, via the reinforcement shield, to the perineum.

12. The perineal protection device of claim 11, wherein the heating apparatus is actuated by a controller responsively to a detection of perineal deformation or shear force.

13. The perineal protection device of claim 1, wherein further comprising an actuator that is controlled by a controller; wherein the actuator provides for changing the mechanical characteristic of at least one of the protective shield or the support pad; and wherein the mechanical characteristics is selected from stiffness, elasticity, flexibility, shape, thickness, or geometric contour.

14. The perineal protection device of claim 13, wherein the at least one mechanical characteristic is controlled by a controller based on signals received by the at least one sensor.

15. The perineal protection device of claim 1, further comprising a sensor for monitoring a characteristic of the perineum comprising tissue thickness of tissue selected from: the underlying subcutaneous perineal tissue, the anal sphincter, or the pelvic floor.

16. The perineal protection device of claim 1, wherein the at least one sensor is configured for monitoring at least one characteristic of the perineum selected from: temperature, normal stress, subcutaneous tissue thickness, or perineal deformation.

17. The perineal protection device of claim 1 wherein the reinforcement fibers are arranged according to at least one of:
   a) a repeating pattern; or
   b) a non-repeating pattern; or
   c) mesh-like structure; or
   d) 'X' shape; pr
   e) Figure "8"'; or
   f) Sinusoidal; or
   g) wave-like; or
   h) saw tooth pattern.

18. The perineal protection device of claim 1 wherein the perineal reinforcement shield and the support pad are at least partially integrally formed with each other.

19. The perineal protection device of claim 1 wherein the perineal reinforcement shield and the support pad comprise various layers.

20. A method for protecting a perineal area with the device of claim 1, the method comprising
   a) securely coupling a perineal protection device with the perineal area of a subject;
   wherein the support pad is securely coupled to the subject, and then the reinforcement shield is securely coupled onto the support pad;
   b) sensing at least one characteristic of the underlying perineal area including shear forces acting on the perineal area; and
   c) wherein based on the at least one sensed characteristic of the underlying perineal area providing for controlling at least one of an actuator or an electroactive material of the perineal protection device to control at least one mechanical characteristic of the perineal device selected from: stiffness, elasticity, flexibility, shape, thickness, or geometric contour.

* * * * *